(12) United States Patent
Perschbacher et al.

(10) Patent No.: US 11,504,537 B2
(45) Date of Patent: Nov. 22, 2022

(54) SYSTEMS AND METHODS FOR DETECTING CHRONIC CARDIAC OVER-PACING

(71) Applicant: Cardiac Pacemakers, Inc., St. Paul, MN (US)

(72) Inventors: David L. Perschbacher, Coon Rapids, MN (US); James O. Gilkerson, Stillwater, MN (US); Sunipa Saha, Shoreview, MN (US); Deepa Mahajan, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 760 days.

(21) Appl. No.: 16/263,736

(22) Filed: Jan. 31, 2019

(65) Prior Publication Data
US 2019/0232065 A1  Aug. 1, 2019

Related U.S. Application Data

(60) Provisional application No. 62/625,168, filed on Feb. 1, 2018.

(51) Int. Cl.

| | |
|---|---|
| *A61N 1/365* | (2006.01) |
| *A61B 5/00* | (2006.01) |
| *A61N 1/39* | (2006.01) |
| *A61B 5/021* | (2006.01) |
| *A61B 5/0245* | (2006.01) |
| *A61N 1/37* | (2006.01) |
| *A61B 5/349* | (2021.01) |
| *A61B 5/0205* | (2006.01) |

(Continued)

(52) U.S. Cl.
CPC .......... *A61N 1/36592* (2013.01); *A61B 5/021* (2013.01); *A61B 5/0245* (2013.01); *A61B 5/349* (2021.01); *A61B 5/4848* (2013.01); *A61B 5/686* (2013.01); *A61B 5/7264* (2013.01); *A61B 5/7275* (2013.01); *A61N 1/3706* (2013.01); *A61N 1/3904* (2017.08); *A61B 5/0006* (2013.01); *A61B 5/0031* (2013.01); *A61B 5/0205* (2013.01); *A61B 5/352* (2021.01); *A61B 7/026* (2013.01); *A61B 2505/07* (2013.01); *A61N 1/046* (2013.01); *A61N 1/3925* (2013.01)

(58) Field of Classification Search
CPC .. A61N 1/36592; A61N 1/3904; A61B 5/021; A61B 5/0205; A61B 5/7275
See application file for complete search history.

(56) References Cited

U.S. PATENT DOCUMENTS

| | | | | |
|---|---|---|---|---|
| 5,040,534 A | * | 8/1991 | Mann | ................. A61N 1/36542 607/19 |
| 2017/0296827 A1 | * | 10/2017 | Yoon | .................... A61N 1/3931 |

* cited by examiner

*Primary Examiner* — Joseph M Dietrich
(74) *Attorney, Agent, or Firm* — Schwegman Lundberg & Woessner, P.A.

(57) ABSTRACT

Systems and methods for monitoring chronic over-pacing (COP) to the heart are discussed herein. In an embodiment, a system includes a receiver circuit to receive information about pacing rates of a plurality of paced heart beats, and a pacing analyzer circuit to generate a pacing rate distribution using pacing rates of the plurality of the paced heart beats. The pacing rate distribution includes a pacing rate histogram. The pacing analyzer circuit may recognize a morphological pattern from the pacing rate distribution, and detect a COP indication using the extracted feature. A programmer circuit adjusts one or more therapy parameters in response to the detected. COP indication.

20 Claims, 7 Drawing Sheets

(51) Int. Cl.
*A61N 1/04* (2006.01)
*A61B 7/02* (2006.01)
*A61B 5/352* (2021.01)

SYSTEMS AND METHODS FOR DETECTING CHRONIC CARDIAC OVER-PACING

CLAIM OF PRIORITY

This application claims the benefit of priority under 35 U.S.C. § 119(e) of U.S. Provisional Patent Application Ser. No. 62/625,168, filed on Feb. 1, 2018, which is herein incorporated by reference in its entirety.

TECHNICAL FIELD

This document relates generally to medical devices, and more particularly, to systems, devices and methods for detecting chronic over-pacing of a heart.

BACKGROUND implantable medical devices (IMDs) have been used for monitoring patient health condition or disease states and delivering therapies. For example, implantable cardioverter-defibrillators (ICDs) are used to monitor certain abnormal heart rhythms. Some IMDs may be used to monitor progression of a chronic disease, such as worsening of cardiac performance due to congestive heart failure (CHF). In addition to diagnostic capabilities, the IMDs may also provide therapies to treat or alleviate certain medical conditions, such as cardiac pacing therapies to treat cardiac arrhythmias or to rectify cardiac dyssynchrony in CHF patients.

IMDs with pacing capabilities may deliver cardiac pacing according to device settings that determine the conditions under which the pacing may be initiated or terminated, pacing configurations such as heart chambers or target sites where the pacing pulses may be delivered, and pacing parameters such as pacing rate and pacing intensity. The IMDs may monitor patient cardiac activities to detect physiological events, such as a cardiac arrhythmia or worsening heart failure (WHF). The IMDs may be interconnected to a patient management system via a data communication network. Device data, such as the medical data associated with the detected physiological events, may be transmitted to a patient management system, through which a healthcare professional may remotely follow up with the patients or assess functions of the IMDs on a regular basis.

OVERVIEW

Ambulatory medical device (AMDs), such as an IMD, have been used to treat various diseases or chronic conditions by delivering electrostimulation. For example, some AMDs may deliver cardiac pacing to treat heart diseases such as cardiac arrhythmias or congestive heart failure, or to prevent certain medical events such as syncope or heart failure decompensation. The AMDs may monitor progression of cardiac disease, and deliver cardiac pacing according to device settings such as programmed by a user (e.g., a clinician).

Efficacy of cardiac pacing therapy may be affected by device settings, such as parameters that control the timing and manner of therapy delivery, or parameters that control the detection of a medical event (e.g., an arrhythmia or a WHF event) that may trigger therapy delivery. Inappropriate therapy delivery or inappropriate detection of medical events may result in undesired consequences, such as over-pacing that lasts for a substantial period of time in some patients, which is referred to as chronic over-pacing (COP) in this document. A number of pacing parameters may affect the timing or manner of pacing delivery. One example of such pacing parameters is a lower rate limit (LRL), representing a base rate at which a pacemaker paces an atrium or a ventricle in the absence of sensed intrinsic cardiac activity or sensor-controlled pacing at a higher rate. Another parameter for pacing control is a maximum tracking rate (MTR). For a pacemaker programmed to VDD or DDD mode, MTR determines the maximum rate at which ventricular pacing will track one-to-one with atrial sensed events. Yet another pacing control parameter is a maximum sensor rate (MSR), which determines the maximum pacing rate as a result of sensor control (e.g., an accelerometer for sensing physical activity, an accelerometer for sensing respiratory rate, or a combination of these sensors). When one or more pacing control parameters are not properly programmed (e.g., the MTR or MSR that is set at a very high level), COP is likely to occur.

Some AMDs include one or more sensors to sense patient metabolic demand or a change thereof, such as a change in respiration rate or ventilation, or an change in physical activity level. An AMD can adjust cardiac pacing (e.g., pacing rate) based on the sensor-indicated changes in metabolic demand. However, efficacy of a sensor-indicated pacing system may be affected by the sensitivity and specificity of the sensors in detecting changes in patient metabolic demand, as well as the amount and the manner of adjustment of cardiac pacing relative to the sensed change in metabolic demand, also known as sensor response factors. In some patients, inappropriate programming of sensor response factors may result in COP.

Chronic over-pacing may also occur as a result of inappropriate detection of a medical event that triggers a change of device operation state, such as a pacing mode in the AMD. Some AMDs can be programmed to initiate or adjust cardiac pacing in response to a change in patient health condition, such as a detection of a cardiac arrhythmia. For example, a mode-switching feature may be used to alleviate symptoms related to tracking of atrial arrhythmias. Generally, ventricular pacing is tracked under a sinus rhythm or sinus tachycardia to provide physiologic pacing and to maintain atrioventricular synchrony. However, when patient develops a pathological atrial arrhythmia (e.g., atrial fibrillation), ventricular pacing stops tracking atrial fibrillation, as doing so may result in inappropriately rapid or irregular ventricular pacing. In response to a detection of atrial arrhythmia, the mode-switching feature is activated, and ventricular pacing may be changed from a tracking mode to a non-tracking mode. In some patients, under-detection of an atrial arrhythmia may withhold or delay effective mode switching, resulting in COP undetected or unknown to a healthcare provider.

Conventional AMDs do not monitor for COP, such that over-pacing of one or more cardiac sites may persist undetected for an extended period time. Without a device alert, healthcare providers may not timely recognize an ongoing COP unless symptoms have developed. Extended pacing at high rates can have long-term consequences to patient cardiac and overall health. For example, unmanaged or untreated COP may cause dyssynchrony, deteriorate cardiac hemodynamic performance, and cause or exacerbate heart failure. Additionally, COP may substantially consume device power, thus reduce the battery life and AMD longevity. The present inventors have recognized that there remains an unmet need for systems and methods to monitor for COP, and timely adjust device settings to prevent exacerbation that COP may cause.

This document discusses, among other things, systems, devices, and methods for monitoring cardiac pacing to detect chronic over-pacing to the heart. An embodiment of a system comprises a receiver circuit to receive information about pacing rates of a plurality of paced heart beats. A pacing analyzer circuit may be configured to generate a pacing rate distribution using the received pacing rate information. The pacing analyzer circuit may extract a feature, such as a morphological pattern, from the pacing rate distribution, and detect a chronic over-pacing (COP) indication using the extracted feature. The system may include a programmer circuit to adjust therapy in response to the detected COP indication.

Example 1 is a system for managing cardiac pacing in a patient. The system comprises a receiver circuit to receive pacing rates of paced heart beats, and a pacing analyzer circuit configured to generate a pacing rate distribution using the received pacing rates, extract a feature from the generated pacing rate distribution, and detect a chronic over-pacing (COP) indication using the extracted feature.

In Example 2, the subject matter of Example 1 optionally includes the pacing analyzer circuit that may be configured to generate the pacing rate distribution including a pacing rate histogram representing a relative number of paced heart beats with pacing rates falling into each of a plurality of pacing rate bins.

In Example 3, the subject matter of Example 2 optionally includes extracted feature including a peak density of the pacing rate histogram.

In Example 4, the subject matter of Example 3 optionally includes the pacing analyzer circuit that may be configured to detect the COP indication if the peak density includes at least two histogram peaks.

In Example 5, the subject matter of Example 4 optionally includes the pacing analyzer circuit that may be configured to detect the COP indication if one of the histogram peaks corresponds to a pacing rate bin with a center pacing rate equal to or greater than 100 beats per minute.

In Example 6, the subject matter of any one or more of Examples 2-5 optionally includes the extracted feature including a morphological pattern of one or more histogram peaks.

In Example 7, the subject matter of Example 6 optionally includes the morphological pattern including a slope of the pacing rate histogram across pacing rate bins. The pacing analyzer circuit may be configured to detect the COP using a change in slope direction of the pacing rate histogram.

In Example 8, the subject matter of any one or more of Examples 1-7 optionally includes comprising a control circuit configured to adjust a therapy in response to the detected COP indication. The pacing rates of the paced heart beats may be determined based on a sensor response. The control circuit may be configured to adjust a pacing parameter including a sensor response factor indicative of a degree of pacing rate increase at elevated patient metabolic demand.

In Example 9, the subject matter of Example 8 optionally includes the control circuit that may be configured to reduce the sensor response factor in response to the detected COP indication.

In Example 10, the subject matter of any one or more of Examples 8-9 optionally includes the pacing rates that are determined based on a response to one or more of a physical activity sensor or a respiration sensor.

In Example 11, the subject matter of any one or more of Examples 1-10 optionally includes a control circuit that may be configured to adjust a therapy including adjusting a pacing mode in response to the detected COP indication.

In Example 12, the subject matter of Example 11 optionally includes an arrhythmia detector circuit that may be configured to detect atrial tachyarrhythmia. The control circuit may be configured to switch to a non-atrial-tracking pacing mode in response to a detection of atrial tachyarrhythmia.

In Example 13, the subject matter of Example 12 optionally includes the control circuit that may be configured to adjust one or more parameters for detecting an atrial tachyarrhythmia in response to the detected COP indication.

In Example 14, the subject matter of any one or more of Examples 1-13 optionally includes the receiver circuit that may further receive information about patient physical activity during the cardiac pacing. The pacing analyzer circuit may be configured to correlate the pacing rate distribution with the information about patient physical activity. The system may include a control circuit configured to adjust the therapy further using the correlation between the pacing rate distribution and the information about patient physical activity.

In Example 15, the subject matter of any one or more of Examples 1-14 optionally includes an electrostimulation circuit that may be configured to generate and deliver the adjusted therapy including a cardiac pacing therapy to the patient.

Example 16 is a method for managing cardiac pacing using a cardiac monitoring system. The method comprises steps of: receiving pacing rates of paced heart beats; generating a pacing rate distribution using the received pacing rates; extracting a feature from the generated pacing rate distribution; and detecting chronic over-pacing (COP) indication using the extracted feature.

In Example 17, the subject matter of Example 16 optionally includes the pacing rate distribution including a pacing rate histogram representing a relative number of paced heart beats with pacing rates falling into each of a plurality of pacing rate bins.

In Example 18, the subject matter of Example 17 optionally includes extracting the feature including a peak density of the pacing rate histogram, and detecting the COP indication if the peak density includes at least two histogram peaks.

In Example 19, the subject matter of any one or more of Examples 17-18 optionally includes extracting the feature including a morphological pattern of one or more histogram peaks.

In Example 20, the subject matter of Example 19 optionally includes the morphological pattern including a slope of the pacing rate histogram across pacing rate bins, and detecting the COP using a change in slope direction of the pacing rate histogram.

In Example 21, the subject matter of any one or more of Examples 16-20 optionally includes receiving the pacing rates of the paced heart beats including sensor-indicated pacing rates according to a sensor response factor indicative of a degree of pacing rate increase at elevated patient metabolic demand, and adjusting a therapy including reducing the sensor response factor in response to the detected COP indication.

In Example 22, the subject matter of any one or more of Examples 16-21 optionally include detecting an atrial tachyarrhythmia, and switching to a non-atrial-tracking pacing mode in response to a detection of atrial tachyarrhythmia.

In Example 23, the subject matter of any one or more of Examples 16-22 optionally includes receiving information about patient physical activity during the cardiac pacing computing a correlation between the pacing rate distribution and the information about patient physical activity, and adjusting a therapy using the correlation between the pacing rate distribution and the information about patient physical activity.

The monitoring of cardiac pacing to detect extended pacing at elevated rate may improve functionality of a medical device such as an AMD. As previously discussed, COP may substantially consume device power, reduce AMD longevity, and have long-term clinical and economic impact on patient management. Systems and methods for detecting and correcting COP as discussed in this document may prevent the battery drain through extended undesirable pacing, and thereby extending the battery efficacy and device longevity. Timely and effective recognition of COP also improves the medical technology of cardiac pacing such as provided by an ambulatory device. As discussed previously, unmanaged or untreated COP may cause dyssynchrony, deteriorate cardiac hemodynamic performance, and cause or exacerbate heart failure, thereby increasing the overall healthcare cost. Compared to the conventional AMDs that lack adequate COP detection and management, the devices and methods discussed herein may improve the pacing therapy and prevent detrimental outcome attributable to COP. Additionally, the COP detection discussed herein is based on a distribution of pacing rate. As cardiac pacing rate is a fundamental measurement of a cardiac monitor, the systems and methods discussed herein require little to no additional cost or system complexity compared to convention technology.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring chronic over-pacing (COP) to the heart. In a system embodiment, a receiver circuit receives information about pacing rates of a plurality of paced heart beats. A pacing analyzer circuit generates a pacing rate distribution using the received information about pacing rates of the plurality of the paced heart beats. The pacing rate distribution may include a pacing rate histogram. The pacing analyzer circuit may recognize a morphological pattern from the pacing rate distribution, and detect a COP indication using the extracted feature. A programmer circuit may adjust therapy in response to the detected COP to prevent future COP and to improve pacing therapy efficacy.

Figure 1:
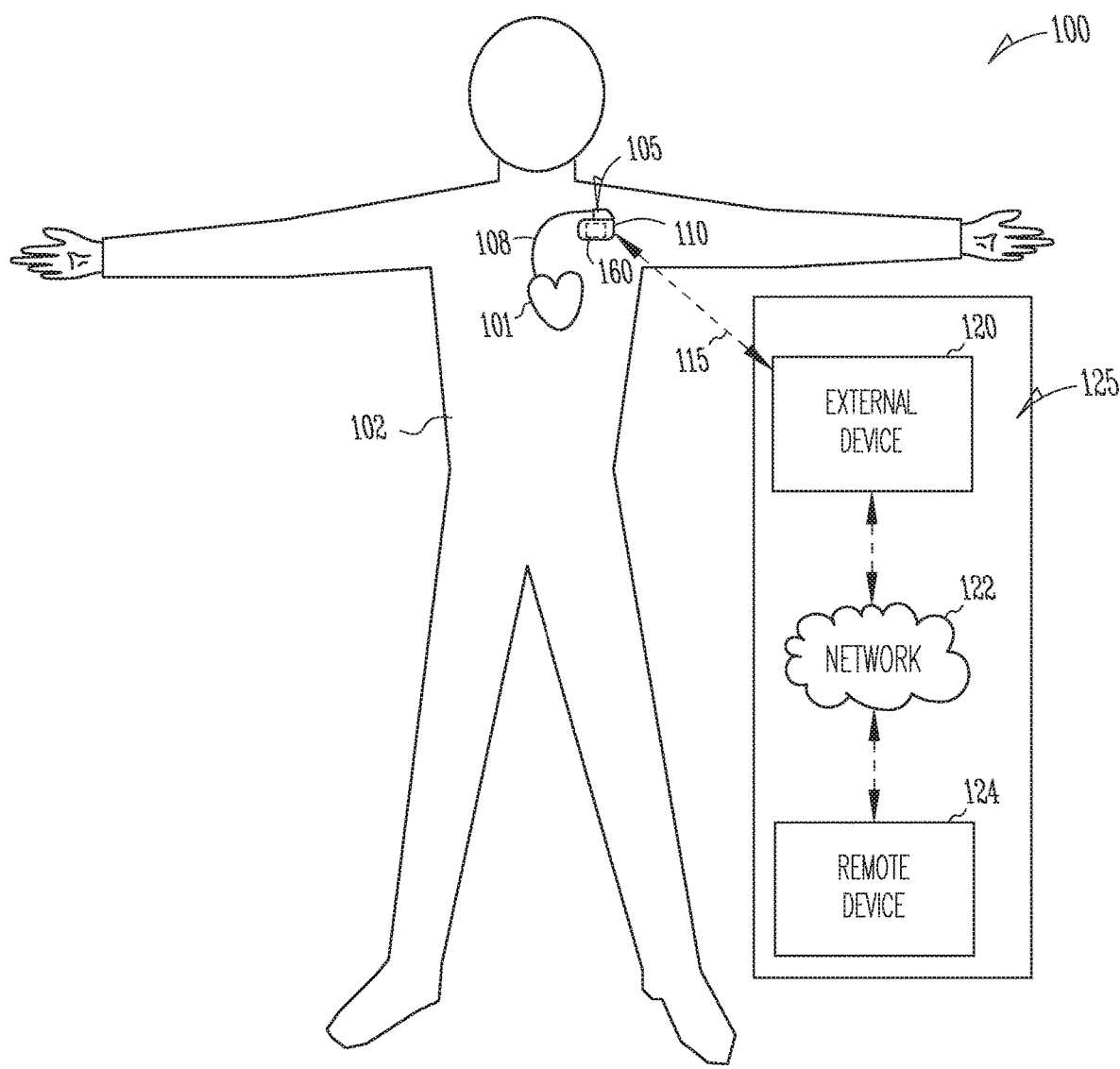
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125. The ambulatory system 105 may include an ambulatory medical device (AND) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the ambulatory system 105 may include one or more leadless sensors not being tethered to the AMD 110 via the lead system 108. The leadless ambulatory sensors may be configured to sense a physiological signal and wirelessly communicate with the AMD 110.

The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. Examples of the physiological signal may include one or more of electrocardiogram, intracardiac electrogram, arrhythmia, heart rate, heart rate variability intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature.

The AMD 110 may include a therapy circuit that may generate and deliver one or more therapies to treat arrhythmia or other heart conditions. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmias, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmias or complications from arrhythmias.

As illustrated in FIG. 1, the AMD 110 may include a therapy control circuit 160 that controls the therapy delivery according to one or more programmable therapy parameters. In an example, the therapy control circuit 160 may control cardiac pacing according to one or more pacing parameters, such as LRL, MSR, MTR, or a pacing mode (e.g., DDD, DDI, or VVI modes, among others). The pacing parameters may be determined or adjusted in response to a detection of chronic over-pacing (COP) using one or more physiological signals sensed from the patient. In an example, COP may be detected in the external system 125, such as by the external device 120 or the remote device 124. Alternatively, COP may be detected within the AMD 110. The COP detection may involve recognition of a characteristic morphological pattern from a pacing rate distribution of a plurality of paced heart beats, which is to be discussed in the following with reference to FIGS. 2-3. The therapy control circuit 160 may control the delivery of pacing using the adjusted therapy parameter to prevent future COP and to improve pacing therapy efficacy.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring medical data, performing at least one self-diagnostic test (such as for a device operational status), analyzing the medical data to detect a cardiac event (e.g., cardiac arrhythmias or worsening of HF), or delivering or adjusting a therapy to the patient 102. Additionally, the external system 125 may receive device data from the AMD 110 via the communication link 115. Examples of the device data received by the external system 125 may include real-time or stored medical data from the patient 102, diagnostic data such as detection of cardiac arrhythmias or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device. The remote device 124 may be configured to evaluate collected patient data and provide alert notifications, among other possible functions. In an example, the external device 120 or the remote device 124 may be configured to detect chronic over-pacing (COP) using information of heart rates of a plurality of paced heart beats, such as sensed by the AMD 110. The COP detection may involve recognition of a characteristic morphological pattern from a pacing rate distribution of the paced heart beats.

The remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. Alternatively or additionally, the alert conditions may be evaluated by the AMD 110. By way of example, alert notifications may include a. Web page update, phone or pager call, E-mail, SMS, text or "Instant" message, as well as a message to the patient and a simultaneous direct notification to emergency services and to the clinician. Other alert notifications are possible.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 124, including the server and the interconnected clients, may also execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected physiological events to a system user such as the patient or a clinician, or to a process including, for example, an instance of a computer program executable in a microprocessor. In an example, the process may include an automated generation of recommendations for anti-arrhythmic therapy, or a recommendation for further diagnostic test or treatment. In an example, the external device 120 or the remote device 124 may include a respective display unit for displaying the physiological or functional signals, or alerts, alarms, emergency calls, or other forms of warnings to signal the detection of arrhythmias. In some examples, the external system 125 may include an external data processor configured to analyze the physiological or functional signals received by the AMD 110, and to confirm or reject the detection of arrhythmias. Computationally intensive algorithms, such as machine-learning algorithms, may be implemented in the external data processor to process the data retrospectively to detect cardiac arrhythmias.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
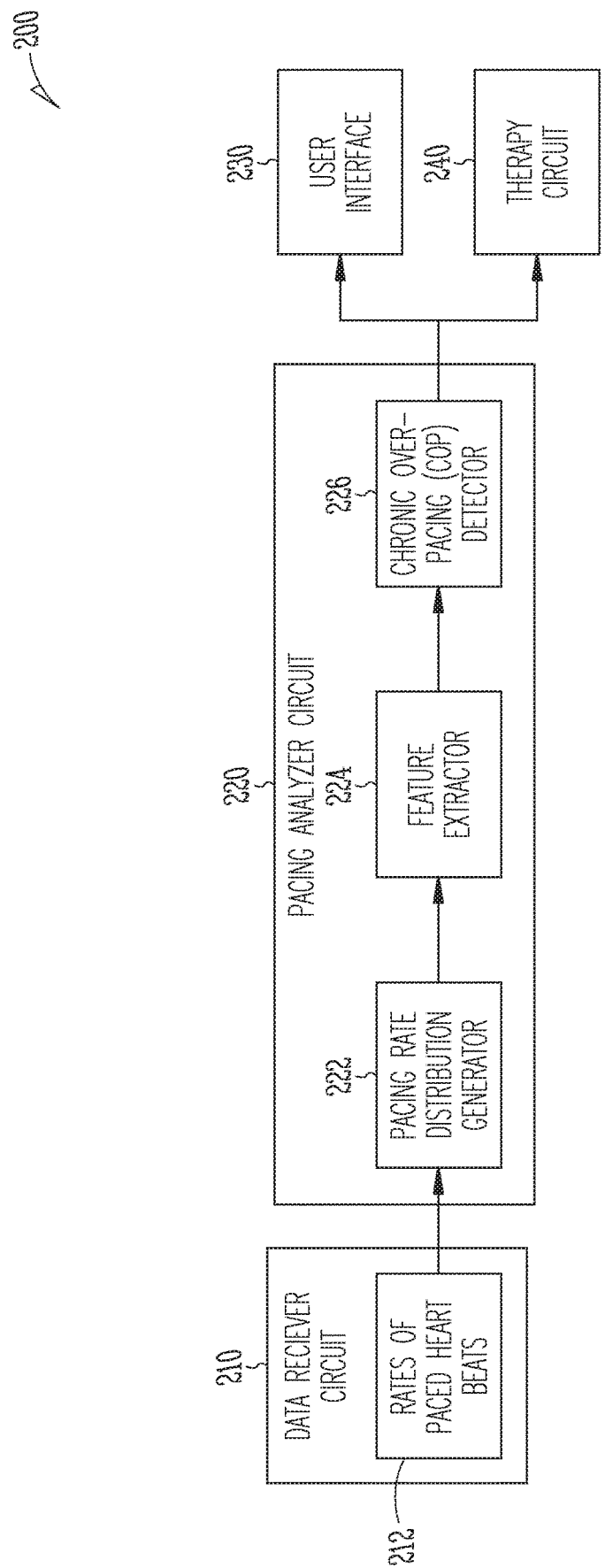
FIG. 2 illustrates generally an example of a cardiac rhythm management system for detecting chronic overpacing (COP) and adjusting pacing accordingly.

FIG. 2 illustrates generally an example of a cardiac rhythm management system 200 for detecting chronic over-pacing (COP) and adjusting pacing accordingly. At least a portion of the cardiac rhythm management system 200 may be implemented in the AMD 110, the external system 125 such as one or more of the external device 120 or the remote device 124, or distributed between the AMD 110 and the external system 125. The cardiac rhythm management system 200 may be configured as a cardiac monitor, including one or more of a data receiver circuit 210, a pacing analyzer circuit 220, and a user interface 230. The cardiac rhythm management system 200 may alternatively be configured as a therapeutic system, which further includes a therapy circuit 260 for delivering a therapy to treat a disease or to alleviate a medical condition.

The data receiver circuit 210 may receive heart rates of a plurality of paced heart beats 212. In an example, the data receiver circuit 210 may include a sensing circuit to sense medical data including one or more physiological signals via one or more implantable, wearable, or otherwise ambulatory sensors or electrodes associated with the patient. The sensors may be incorporated into, or otherwise associated with an ambulatory device such as the AMD 110. Examples of the physiological signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others, The data receiver circuit 210 may include one or more sub-circuits to digitize, filter, or perform other signal conditioning operations on the received physiological signal. In some examples, the physiological signals sensed from a patient may be stored in a storage device, such as an electronic medical record (EMR) system. The detector circuit may be configured to receive a physiological signal from the storage device in response to a user input or triggered by a specific event. The data receive circuit 210 may measure heart rates of a plurality of paced heart beats 212 from the received physiologic signals.

The pacing analyzer circuit 220 may analyze the pacing rates to detect chronic over-pacing (COP) at one or more cardiac sites, such as chronic atrial over-pacing or chronic ventricular over-pacing. The pacing analyzer circuit 220 may be implemented as a part of a microprocessor circuit, which may be a dedicated processor such as a digital signal processor, application specific integrated circuit (ASIC), microprocessor, or other type of processor. Alternatively, the microprocessor circuit may be a general purpose processor that may receive and execute a set of instructions of performing the functions, methods, or techniques described herein.

The pacing analyzer circuit 220 may include circuit sets comprising one or more other circuits or sub-circuits, including a pacing rate distribution generator 222, a feature extractor 224, and a COP detector 226. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The pacing rate distribution generator 222 may generate a pacing rate distribution using the pacing rates of the paced heart beats. The pacing rate distribution represents frequencies of various pacing rates or ranges of pacing rate. In an example, the pacing rate distribution may be generated when sufficient amount of paced heart beats are collected, such as greater than or equal to a specified minimum beat number (e.g., approximately 80,000 to 100,000 beats) or for at least a specified minimum time duration (e.g. 12 or 24 hours). The pacing rate distribution generated from sufficient amount of heart beats may provide a more reliable estimate of frequencies of various pacing rates or ranges of pacing rate. In an example, to reduce computation complexity, the amount of heart beats used for computing the pacing rate distribution may be limited to no greater than a specified maximum beat number or no collected no longer than a specified maximum time period (e.g. 5-7 days). The pacing rate distribution generator 222 may update the pacing rate distribution continuously to incorporate more paced heart beats as they become available. Alternatively, the update of the pacing rate distribution may be periodic, such as every day or every week. In some examples, the update of the pacing rate distribution may be performed in a command mode, such that a user (e.g., a clinician) may specify the paced heart beats to generate the pacing rate distribution. For example, during a patient follow-up visit, a clinician may reset the pacing rate distribution, such as by clearing, adding, or otherwise modifying the paced heart beats for establishing the pacing rate distribution.

In an example, the pacing rate distribution may include a pacing rate histogram representing a relative number of paced heart beats with pacing rates falling into each of a plurality of pacing rate bins (i.e., ranges of pacing rate), or accumulated time spend on each of the plurality of pacing rate bins. The pacing rate bin may have a programmable size. In an example, the pacing rate bin has a size of approximately 10 beats per minute (bpm).

The feature extractor 224 may extract a feature from the pacing rate distribution. By way of example and not limitation, the extracted feature may include a morphological feature of the pacing rate histogram. The COP detector 226 may detect COP using at least the extracted feature of the pacing rate distribution, such as a morphologic feature from the pacing rate histogram. In an example, the morphological feature may include a peak density of the pacing rate histogram. The peak density refers to the number of peaks in the pacing rate histogram. The present inventors have recognized that in the absence of COP, generally only one peak is presented in the pacing rate histogram. Two or more peaks in the pacing rate histogram may indicate a presence of COP. The COP detector 226 may be configured to detect the COP indication if at least two histogram peaks are detected from the pacing rate histogram. A histogram peak is detected if it satisfies an absolute amplitude requirement, such as exceeding an amplitude threshold. As the peak amplitude in a pacing rate histogram represents the frequency of paced beats or the accumulated time spent on the pacing rate bins at which the histogram peak is located, the peak amplitude threshold determines the degree of chronicity of cardiac over-pacing. In an example, the amplitude of a histogram bin is represented by a percentage of beats being analyzed that fall within the heart rate range of the histogram bin, and the amplitude threshold is approximately 2-10%. Additional conditions may be applied to detect a histogram peak. In an example, in addition to the absolute amplitude requirement, a relative amplitude requirement must also be satisfied to be detected as a histogram peak. For example, the amplitude of the histogram bin must exceed the amplitude of neighboring histogram bins by at least a specified margin. In an example, the margin is approximately 1-5%. Generally, the margin for use in the relative amplitude requirement is set to be smaller than the amplitude threshold for use in the absolute amplitude requirement. In various example, a COP is detected if the histogram peaks additionally or alternatively each satisfy a timing requirement, such that the two histogram peaks are separated by at least a specified pacing rate bins, such as approximately 10-20 bpm. The inter-peak separation may be determined using center pacing rates of the pacing rate bins where the histogram peaks are located. The inter-peak separation requirement as discussed herein may help avoid detection of local histogram peaks due to fluctuations of sensed heart rates. In an example, the COP detector 226 may be configured to detect the COP indication if one of the histogram peaks is located at a center pacing rate exceeding a specified pacing rate, such as equal to or greater than 100 bpm.

In another example, the morphological feature may include a morphological pattern of one or more histogram peaks. The morphological pattern may be represented by a slope of the pacing rate histogram across pacing rate bins. The feature extractor 224 may detect a change in slope direction of the pacing rate histogram. The change in slope direction, such as a change from a positive slope to a negative slope, may indicate a histogram peak. A change from a negative slope to a positive slope may indicate a histogram valley, or a presence of a second histogram peak. In some examples, the feature extractor 224 may interpolate the pacing rate histogram, or to perform curve-fitting on the pacing rate histogram, and extract the feature of the histogram slope from the interpolated or curve-fitted pacing rate histogram. The COP detector 226 may detect the COP based on a change in slope direction of the pacing rate histogram. Examples of the heart rate histograms and morphological features indicative of COP are discussed below, such as with reference to FIGS. 3A-3C.

The user interface 240 may include an input unit and an output unit. In an example, at least a portion of the user interface 240 may be implemented in the external system 125. The input unit may receive user input for programming the pacing analyzer circuit 220, such as parameters and threshold values for detecting COP indications. The input unit may include an input device such as a keyboard, on-screen keyboard, mouse, trackball, touchpad, touchscreen, or other pointing or navigating devices. The output unit may include a display for displaying the patient physiological data, pacing rate distribution, and detection of COP. The output unit may generate a recommendation for adjusting AMD programming based on the detection of COP, such as adjusting one or more pacing parameters or one or more detection parameters for detecting a medical event (e.g., cardiac arrhythmia or worsening of heart failure) that may trigger pacing therapy. The output unit may include a printer for printing hard copies of the detection information. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected medical events.

The therapy circuit 240 may be configured to deliver a therapy to the patient in response to a detection of COP indication. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 240 may modify an existing therapy, such as adjust a stimulation parameter or drug dosage. In an example, the therapy circuit 240 may be coupled to a therapy control circuit that automatically adjust one or more pacing parameters in response to the detection of COP indication, as to be discussed in the following with reference to FIG. 4.

Figure 3A:
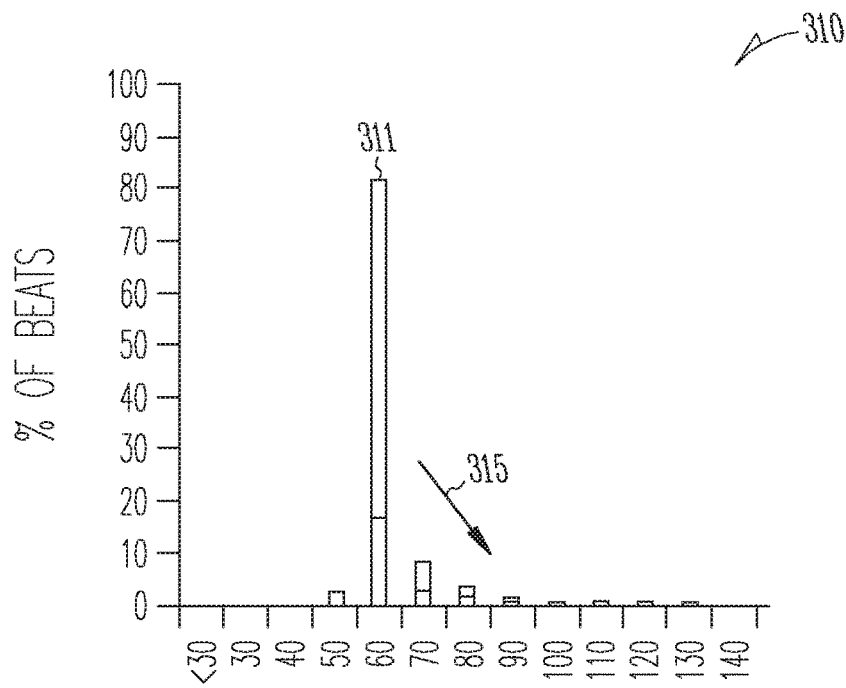
FIGS. 3A-3C illustrate examples of pacing rate histograms under different pacing modes in the presence or absence of chronic over-pacing.
Figure 3B:
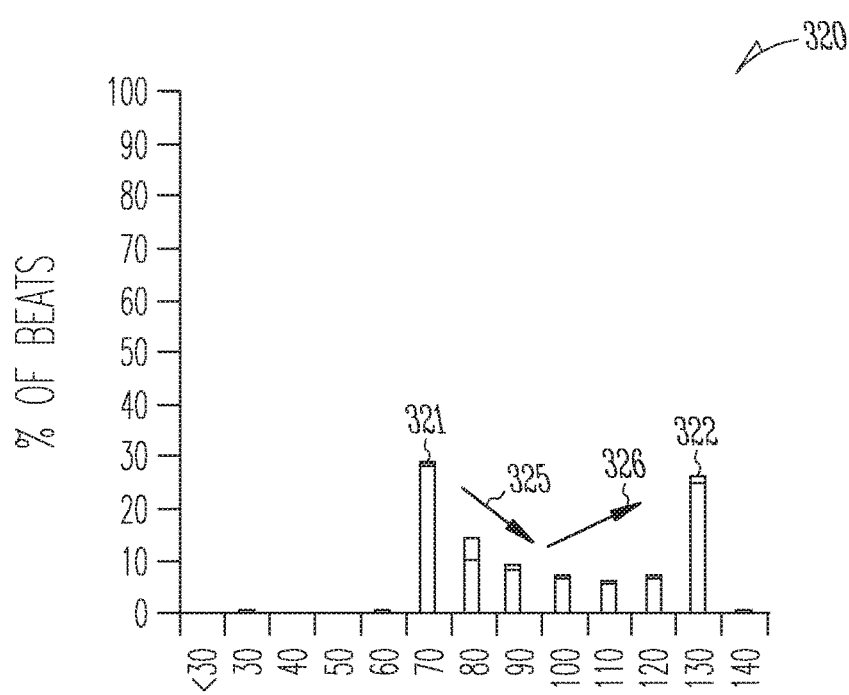
Figure 3C:
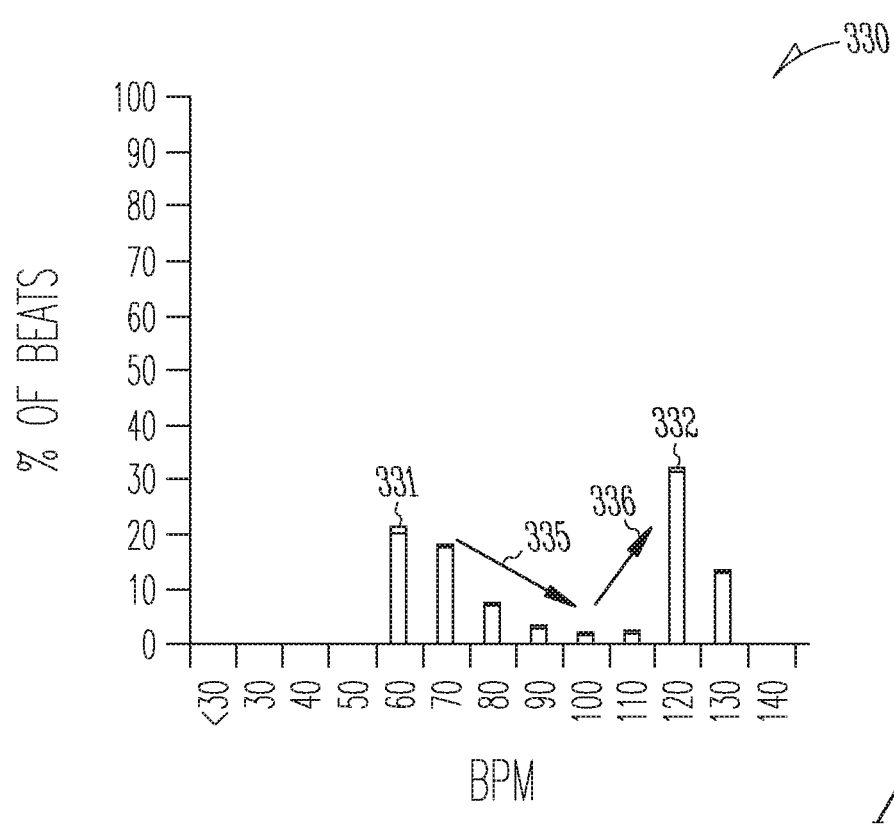

FIGS. 3A-3C illustrate examples of pacing rate histograms 310, 320, and 330 under different pacing states in the presence or absence of chronic over-pacing. The pacing rate histograms may be generated by the pacing rate distribution generator 222, and presented on a display of the user interface 230. FIG. 3A illustrates a ventricular pacing rate histogram 310 in a pacemaker patient free of COP. The histogram 310 has a single histogram peak 311 at 60 bpm, representing pacing at a preset lower rate limit (LRL) of approximately 60 bpm for substantial amount of time. The histogram 310 also has a morphological pattern of monotonic decrease trend 315 of the number of paced beats or accumulated time for higher pacing rate bins greater than 60 bpm. The feature extractor 224 may extract morphological features, such as one or more of the single peak 311, or the monotonic decrease trend 315, and the COP detector 226 may determine that no chronic over-pacing based on the extracted morphological features.

FIG. 3B illustrates an atrial pacing rate histogram 320 indicating presence of chronic over-pacing at a higher pacing rate due to inappropriate programming of sensor response factors. The atrial pacing rates in this example are acquired from a pacemaker programmed to dual-chamber rate responsive pacing mode (DDDR mode). Rate responsive pacing is delivered at sensor-indicated rates. One or more sensors may be used to detect a change in patient metabolic demand, and the pacing rate may be adjusted in accordance with sensor-indicated metabolic demand. One example of such sensors is a thoracic impedance sensor configured to sense respiration, such as a change in minute ventilation (MV). Another example includes an accelerometer (XL) configured to sense patient physical activity level. An increase in respiration rate or MV, and/or an increase in patient physical activity, may indicate an increase in metabolic demand, which may trigger cardiac pacing (e.g., at an atrium) at a higher rate to meet patient metabolic demand. A programmable pacing parameter, sensor response factor, may be defined for each sensor, and controls the pacing rate (or a change in pacing rate) at various sensor response levels. In some examples, two or more sensors (e.g., respiratory sensor or physical activity sensor) may be blended to jointly determine the pacing rate.

As illustrated in FIG. 3B, the histogram 320 has two histogram peaks: a first peak 321 at a pacing rate bin centered at 70 bpm, and a second peak 322 at a pacing rate bin centered at 130 bpm. While the first peak 321 represents pacing at a preset LRL of approximately 70 bpm, the second peak 322 represents a substantial number of atrial pacing beats at a preset maximum sensor rate (MSR) of approximately 130 bpm. In contrast to the one-peak pattern in FIG. 3A, the two histogram peaks shown in histogram 320 is characteristic of chronic over-pacing, which in this case at or near the preset MSR. Over-pacing at MSR may be caused by inappropriate device setting, such as inappropriate MSR level, or inappropriate sensor response factor. For example, when a response factor of a MV sensor or of a physical activity sensor is set to a high level, atrial pacing at the preset MSR is more likely to be delivered even with moderate level of sensor-indicated increase in metabolic demand. The feature extractor 224 may extract morphological features such as the two histogram peaks 321 and 322, or a morphological pattern including a decrease trend 325, followed by an increase trend 326 of the histogram amplitude over the pacing rate bins. In an example, the COP detector 226 may determine that COP has occurred if the two peaks 321 and 322 satisfy the peak amplitude requirement and/or minimum separation of pacing rates requirement between the two peaks. The COP detector 226 may alternatively detect the COP based on the morphological pattern of a decrease trend 325 followed by an increase trend 326 of the histogram amplitude over the pacing rate bins.

FIG. 3C illustrates a ventricular pacing histogram 330 indicating chronic over-pacing at a higher pacing rate due to under-detected atrial tachyarrhythmia. The ventricular pacing rates in this example are acquired from a pacemaker programmed to DDD mode. Ventricular pacing is normally delivered in an atrial tracking mode, such that paced ventricular depolarization tracks one-to-one with non-refractory sensed atrial events. However, when the patient develops an atrial tachyarrhythmia, tracking of the atrial tachyarrhythmia can lead to rapid ventricular pacing and the occurrence of palpitation, dyspnea, chest pain, or lightheadedness. Atrial tachy response (ATR) parameter and mode switch may be used to prevent rapid ventricular pacing in the presence of atrial tachyarrhythmia. For example, when the atrial rate is sufficiently high (e.g., exceeds an atrial rate threshold) and last for sufficiently amount of beats or time (e.g., exceeding a duration threshold value), the ATR may be activated, and the pacing model may be automatically switched to a non-tracking mode (e.g., DDI(R) or VDI(R) mode). Accurate and timely detection of rapid atrial rate (e.g., atrial tachyarrhythmia) can be crucial for prompt mode switch. However, if ATR parameters (e.g., atrial tachy rate threshold, or duration threshold) are inappropriately programmed, under-detection or delayed detection of atrial tachyarrhythmia may happen, causing no or delayed ATR mode switch. As a result, ventricular pacing may continue at high rates to track the undetected atrial tachyarrhythmia. The histogram 330 illustrates such a scenario where an atrial tachyarrhythmia is slower that a preset ATR rate of approximately 170 bpm. The second histogram peak at a pacing rate of approximately 120 bpm represents chronic ventricular over-pacing due to sustained tracking of atrial tachyarrhythmia without being detected due to inappropriate device setting, such as ATR parameters for atrial tachyarrhythmia detection. The feature extractor 224 may extract morphological features such as the two histogram peaks 331 and 332, or a morphological pattern including a decrease trend 335, followed by an increase trend 336 of the histogram amplitude over the pacing rate bins. The COP detector 226 may determine an occurrence of COP if the two peaks 331 and 332 satisfy peak amplitude requirement and/or requirement for a separation of central pacing rates of the two peaks. Alternatively, the COP detector 226 may detect COP based on the morphological pattern of a decrease trend 335 followed by an increase trend 336 over the pacing rate bins.

Figure 4:
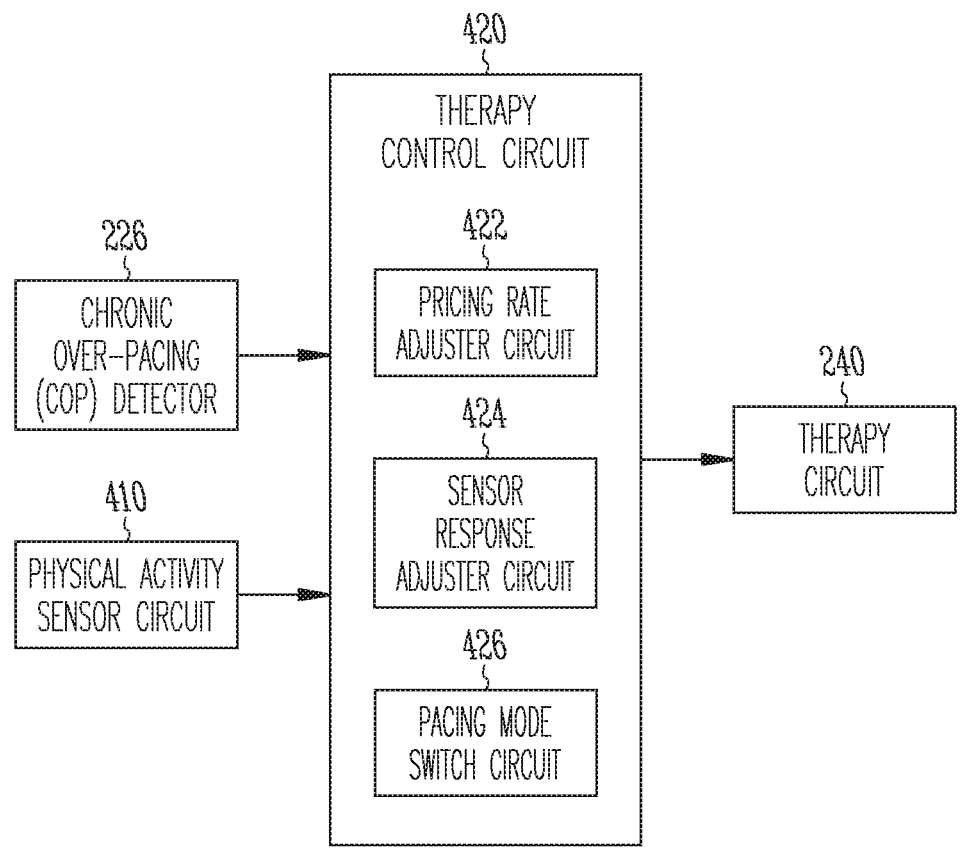
FIG. 4 illustrates a portion of a cardiac pacing system for titrating pacing therapy based at least one the detection of COP.

FIG. 4 illustrates a portion of a cardiac pacing system 400 for titrating pacing therapy based at least on the detection of COP. At least a portion of the cardiac pacing system 400 may be implemented in the cardiac rhythm management system 200. The cardiac pacing system 400 may include a COP detector 226, an optional physical activity sensor circuit 410, a therapy control circuit 420, and a therapy circuit 240. As previously discussed with reference to FIG. 2, the COP detector 226 may, generate a COP indicator using features extracted of the pacing rate distribution, such as a morphologic feature from the pacing rate histogram. The therapy control circuit 420 may titrate pacing therapy, such as by adjusting one or more pacing parameters, based at least on the detection of COP. In an example, the therapy control circuit 420 may be included in a programmer device in the external device 120. Therapy titration may include an adjustment of pacing site or pacing vector configuration (e.g., anode and cathode electrodes), or an adjustment of pacing strength that determines amount of energy delivered to the pacing site such as pulse amplitude, pulse width, pulse frequency, pulse waveform, duty cycle, or pacing duration, among other parameters. Therapy titration may alternatively or additionally include adjustment of pacing timing parameters that determine the timing and sequence of pacing pulses, such as atrial-ventricular delay (AVD) representing a latency period between an atrial activation (intrinsic or paced activation) and ventricular pacing, an interventricular pacing delay (VVD) representing a time delay between ventricular pacing at the left and right ventricles, or intraventricular pacing delay representing a time delay between pacing at multiple site of a ventricle. The therapy circuit 240 generate and deliver cardiac pacing therapy in accordance with the adjusted pacing parameters.

The therapy control circuit 420 may include one or more sub-circuits to control various aspects of pacing therapy. Alternatively, the therapy control circuit 420 may be implemented as a part of a microprocessor circuit that may receive and execute a set of instructions of performing pacing parameters adjustment described herein. By way of example and not limitation, the therapy control circuit 420 may include one or more of a pacing rate adjuster circuit 422, a sensor response adjuster circuit 424, or pacing mode switch circuit 426. The pacing rate adjuster circuit 422 may reduce pacing rate in response to the detection of COP. In an example, a reduction of pacing rate may be achieved by, for example, reducing the maximum tracking rate (MTR), reducing the MSR, extending AV delay, or extending atrial refractory period, among others. The sensor response adjuster circuit 424 is configured to adjust sensor-indicated pacing rate by modifying a sensor response factor in response to a detection of COP. Sensor-indicated pacing may be used in any adaptive-rate pacing modes (i.e., any mode ending with "R", such as DDDR, VVIR, AAIR modes), where one or more sensors are used to detect changes in patient metabolic demand, and the pacing rate are adjusted accordingly. Examples of the sensors for detecting metabolic demand or a change thereof may include an impedance sensor for sense respiration or minute ventilation, or an accelerometer to sense physical activity, or a blend of sensors. The sensor response factor for a particular sensor determines a pacing rate (above the LRL) at various levels of sensor-indicated metabolic demand. For example, the response factor for accelerometer ($R_{XL}$) maps activity levels (e.g., represented by amplitude and/or frequency of XL signal) to various pacing rates, the sensor response factor for impedance sensor ($R_{MV}$) maps various elevated minute ventilation levels (e.g., represented by a change of thoracic impedance from a baseline level) to various pacing rates. In response to a detection of COP, the sensor response adjuster circuit 424 may reduce the sensor response factor of one or more sensors. As discussed previously with reference to FIG. 3B, if the sensor response factor is set inappropriately high, a moderate elevation of respiration or physical activity may trigger a substantial increase in pacing rate, thereby increasing the chance of pacing at maximum sensor rate (MSR) and resulting in COP. By reducing the sensor response factor, COP at MSR due to moderately elevated metabolic demand may be prevented or reduced.

The pacing mode switch circuit 426 is configured to adjust parameters controlling the ATR mode switch function to improve atrial tachyarrhythmia detection sensitivity, in response to a detection of COP. Examples of the ATR parameter may include atrial tachy detection rate, a duration, an entry count representing a threshold number of fast atrial beats (i.e., atrial beats faster than atrial tachy detection rate) that must be met to initiate the duration, and an exit count representing a threshold number of slow atrial beats (i.e., atrial beats slower than atrial tachy detection rate) that must be met to end the duration, among others. As discussed above with reference to FIG. 3C, COP may be caused by under-detection or delayed detection of atrial tachyarrhythmia, hence no activation or delayed ATR mode switch to a non-tracking pacing mode. To improve the atrial tachy detection sensitivity, the pacing mode switch circuit 426 may reduce one or more of atrial tachy detection rate, duration, entry count, or exit count. With such parameter adjustment, atrial tachyarrhythmia is more likely to be detected, and the pacing mode switch circuit 426 may promptly switch to a non-atrial tracking mode. Accordingly, ventricular COP due to under-detected atrial tachyarrhythmia may be prevented or reduced.

As illustrated in FIG. 4, the cardiac pacing system 400 may include an optional physical activity sensor circuit 410 configured to sense information about patient physical activity during cardiac pacing. The physical activity sensor circuit 410 may be coupled to a physical activity sensor, which can be an implantable, wearable, holdable, or otherwise ambulatory sensor for sensing physical activity. The physical activity sensor may include a single-axis or a multi-axis accelerometer configured to sense an acceleration signal of at least a portion of the subject's body. The strength of the acceleration signal can be indicative of the physical activity level. The pacing analyzer circuit 220 may include a correlator that correlates the pacing rate distribution with patient physical activity levels. The therapy control circuit 420 may adjust the one or more pacing parameters further using the correlation between the pacing rate distribution and patient physical activity. In an example, the sensor response adjuster circuit 424 may adjust an activity sensor-indicated pacing rate by modifying a sensor response factor. Reducing the sensor response factor may help reduce COP when a patient engages in a moderate-intensity physical activity.

Figure 5:
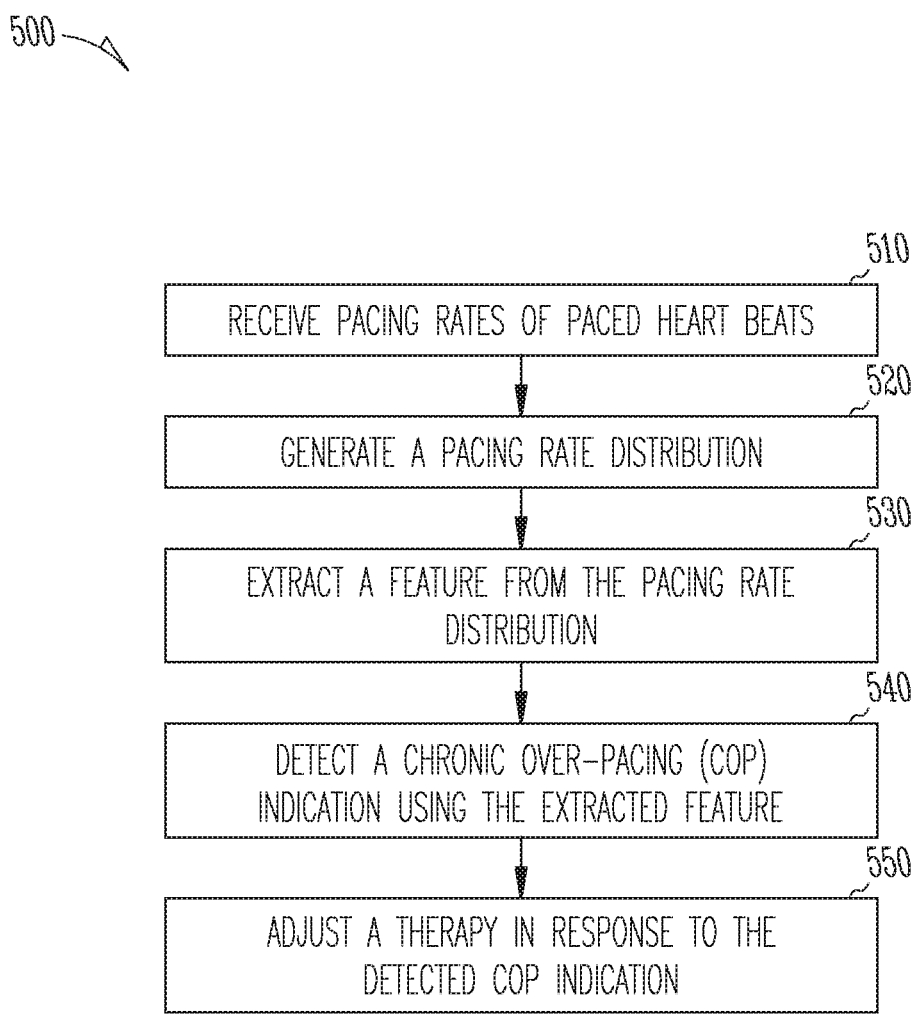
FIG. 5 illustrates generally an example of a method for managing cardiac pacing therapy.

FIG. 5 illustrates generally an example of a method 500 for managing cardiac pacing therapy. Cardiac pacing may be delivered via an ambulatory pacing system, such as the AMD, according to one or more pacing parameters. The pacing parameters may be determined or adjusted in response to a detection of an occurrence of chronic overpacing (COP). The method 500 may be implemented in, and executed by, the AMD 110, one or more devices in the external system 125, or the cardiac rhythm management system 200.

The method 500 commences at 510 to receive pacing rates of paced heart beats. The pacing rates may be detected from a cardiac signal, such as an ECG, an intracardiac EGM of at a cardiac site such as an atrium or a ventricle. At 520, a pacing rate distribution may be generated using the received pacing rates. The pacing rate distribution represents how frequently the various pacing rates or ranges of pacing rate appear in the paced heart beats being analyzed. In an example, the pacing rate distribution includes a pacing rate histogram representing a relative number of paced heart beats with pacing rates falling into each of a plurality of pacing rate bins ranges of pacing rate), or accumulated time spend on each of the plurality of pacing rate bins. The pacing rate bin may have a programmable size.

At 530, a feature may be extracted from the pacing rate distribution, such as using the feature extractor 224. The extracted feature may include a morphological feature of the pacing rate histogram. In an example, the morphological feature may include a peak density of the pacing rate histogram. The peak density may refer to number of peaks in the pacing rate histogram. The present inventors have recognized that two or more peaks in the pacing rate histogram may indicate presence of COP. In another example, the morphological feature may include a morphological pattern of one or more histogram peaks. The morphological pattern may include a slope of the pacing rate histogram across pacing rate bins. A change in slope direction of the pacing rate histogram, such as a change from a positive slope to a negative slope, may indicate a presence of histogram peak. In some examples, interpolation or curve-fitting may be performed on the pacing rate histogram, and a morphological feature (e.g., change of slope direction) may be extracted from interpolated or curve-fitted pacing rate histogram.

At 540, a COP indication may be detected using at least the extracted feature of the pacing rate distribution, such as a morphologic feature extracted from the pacing rate histogram. In an example, a COP is indicated if at least two histogram peaks are detected from the pacing rate histogram. To improve the detection robustness, in an example, a COP is detected if the histogram peaks satisfy an amplitude requirement that the amplitude of the histogram peak exceed a peak amplitude threshold, and/or that the two histogram peaks are separated by at least a specified pacing rate bins, such as approximately 10-20 bpm. In another example, the COP detector 226 may detect the COP indication if one of the histogram peaks corresponds to a pacing rate bin with a center pacing rate exceeding a specified pacing rate, such as equal to or greater than 100 bpm. In yet another example, a COP indication may be detected using a change in slope direction of the pacing rate histogram, such as a decrease trend, followed by an increase trend, of the histogram amplitude over the pacing rate bins, as illustrated in FIGS. 3B-3C.

At 550, a therapy may be adjusted in response to the detected COP indication. Adjusted therapy may be delivered according to the adjusted therapy parameters, in response to a detection of COP indication. Examples of the therapy may include electrostimulation therapy delivered to the heart, a nerve tissue, other target tissues, a cardioversion therapy, a defibrillation therapy, or drug therapy including delivering drug to a tissue or organ. In some examples, information about patient physical activity may be acquired during cardiac pacing. A correlation between the pacing rate distribution and patient physical activity correlation between the pacing rate distribution and patient physical activity may be used to determine therapy adjustment. Therapy adjustment may be carried out automatically by the therapy circuit 420, or with user intervention such as via the user interface 230. In an example, in response to the detection of COP, one or more pacing parameters that control the pacing rate may be adjusted, including reducing MTR, extending AV delay, or extending atrial refractory period, among others. Therapy titration may additionally or alternatively include adjustment of pacing site or pacing vector configuration (e.g., anode and cathode electrodes), pacing strength that determines amount of energy delivered to the pacing site (e.g., one or more of pulse amplitude, pulse width, pulse frequency, pulse waveform, duty cycle, or pacing duration), or pacing timing parameters that determine the timing and sequence of pacing pulses.

In another example, in response to a detection of COP, a sensor response factor may be adjusted to reduce a sensor-indicated pacing rate, as used in any adaptive-rate pacing modes (e.g., DDDR, VVIR, or AAIR mode). The sensor response factor for a particular sensor (e.g., an accelerometer sensor for sensing physical activity levels, or a thoracic impedance sensor for sensing elevated minute ventilation) determines a pacing rate at various levels of sensor-indicated metabolic demand. FIG. 3B illustrated an example that when the sensor response factor is set to an inappropriately high level, a moderate elevation of respiration or physical activity, may trigger a substantial increase in atrial pacing rate, thereby increasing the chance of COP at maximum sensor rate (MSR). By reducing the sensor response factor for one or more sensors, COP at MSR may be prevented or reduced.

In another example, in response to a detection of COP, parameters controlling the ATR mode switch may be adjusted to improve atrial tachyarrhythmia detection. Examples of the ATR parameter may include atrial tachy detection rate, a duration, an entry count representing a threshold number of fast atrial beats (faster than atrial tachy detection rate) that must be met to initiate the duration, and an exit count representing a threshold number of slow atrial beats (slower than atrial tachy detection rate) that must be met to end the duration, among others. FIG. 3C illustrates an example of COP caused by under-detection or delayed detection of atrial tachyarrhythmia, and therefore no activation or delayed activation of ATR mode switch to a non-tracking pacing mode. One or more of atrial tachy detection rate, duration, entry count, or exit count may be reduced to improve sensitivity of the atrial tachyarrhythmia detection, such that ATR mode switch may be promptly activated. Chronic ventricular over-pacing due to under-detected atrial tachyarrhythmia and slowed ATR mode switch may be prevented or reduced.

Figure 6:
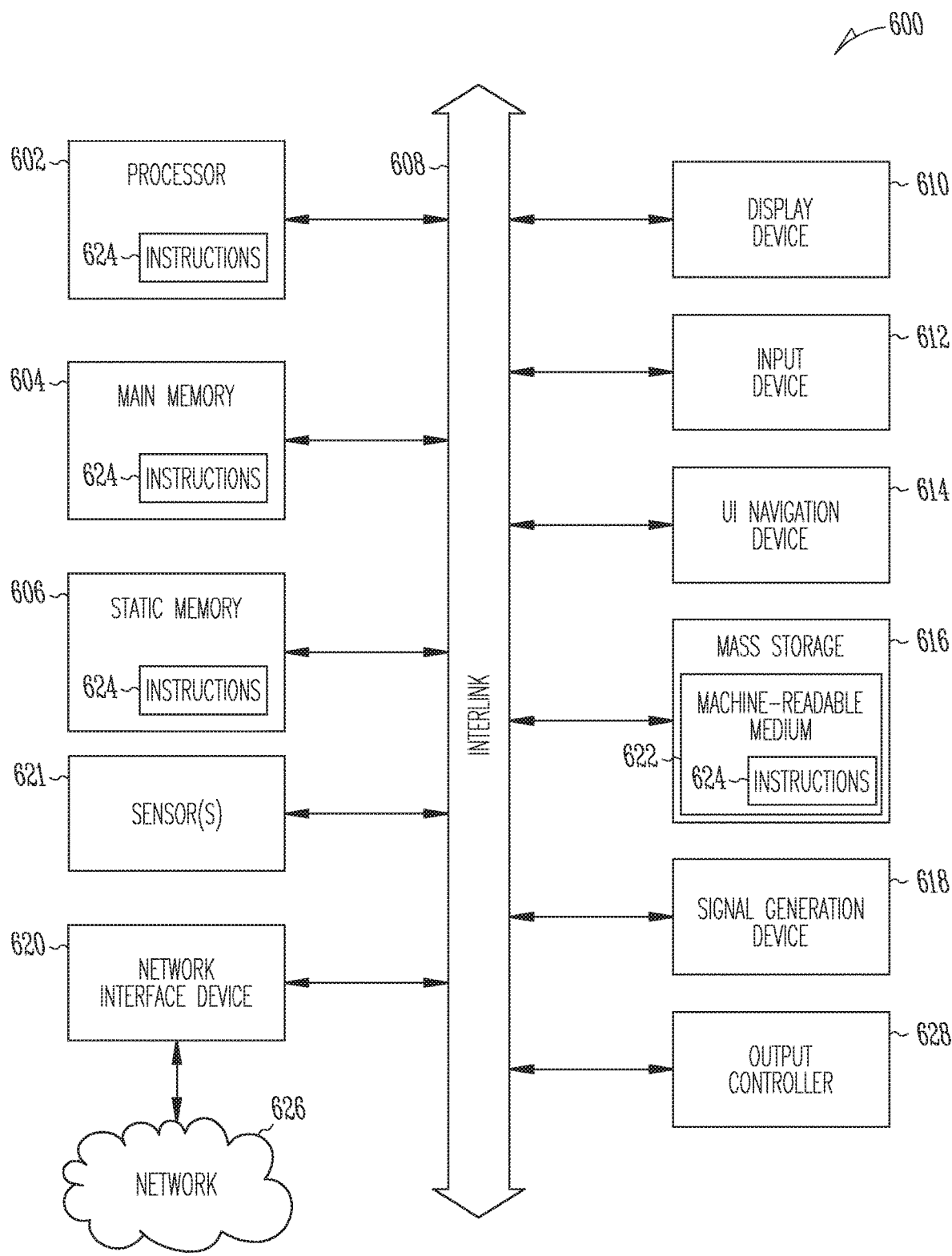
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually, or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communication network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family, of standards; peer-to-peer (P2P) networks, among others. In an example, the network interface device 620 may include one or more physical jacks (e.g., Ethernet, coaxial, or phone jacks) or one or more antennas to connect to the communication network 626. In an example; the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for managing cardiac pacing in a patient; the system comprising:
a pacing analyzer circuit configured to:
receive pacing rates of paced heart beats;
generate a pacing rate distribution using the received pacing rates;
extract a feature from the generated pacing rate distribution; and
detect a chronic over-pacing (COP) indication using the extracted feature, the COP indication indicating pacing at a rate higher than a pre-determined pacing rate threshold above a base pacing rate for an extended time period; and
a control circuit configured to adjust a pacing therapy parameter in response to the detected COP indication.

2. The system of claim 1, wherein the pacing analyzer circuit is configured to generate the pacing rate distribution including a pacing rate histogram representing a relative number of paced heart beats with pacing rates falling into each of a plurality of pacing rate bins.

3. The system of claim 1, wherein the extracted feature includes a peak density of the pacing rate distribution.

4. The system of claim 3, wherein the pacing analyzer circuit is configured to detect the COP indication if the peak density includes at least two peaks in the pacing rate distribution.

5. The system of claim 2, wherein the extracted feature includes a morphological pattern of one or more peaks in the pacing rate distribution.

6. The system of claim 5, wherein the morphological pattern includes a slope of the pacing rate histogram across pacing rate bins, and the pacing analyzer circuit is configured to detect the COP using a change in slope direction of the pacing rate histogram.

7. The system of claim 1, comprising a sensor circuit configured to sense a signal from the patient; wherein the control circuit is configured to determine the pacing rate from the sensed signal, and to adjust the pacing therapy parameter including reducing a sensor response factor in response to the detected COP indication, the sensor response factor indicative of a degree of pacing rate increase at elevated patient metabolic demand.

8. The system of claim 7, wherein the sensor circuit includes one or more of a physical activity sensor or a respiration sensor.

9. The system of claim 1, comprising an arrhythmia detector circuit configured to detect atrial tachyarrhythmia, and a control circuit configured to switch to a non-atrial-tracking pacing mode in response to a detection of atrial tachyarrhythmia.

10. The system of claim 9, wherein the control circuit is configured to adjust one or more parameters for detecting an atrial tachyarrhythmia in response to the detected COP indication.

11. The system of claim 1, wherein the pacing analyzer circuit is further configured to receive information about patient physical activity during the cardiac pacing, and to correlate the pacing rate distribution with the information about patient physical activity.

12. The system of claim 1, comprising an electrostimulation circuit configured to generate and deliver a therapy including a cardiac pacing therapy to the patient in accordance with the adjusted pacing therapy parameter.

13. A method for managing cardiac pacing using a cardiac monitoring system, the method comprising:
receiving pacing rates of paced heart beats;
generating a pacing rate distribution using the received pacing rates;
extracting a feature from the generated pacing rate distribution;
detecting a chronic over-pacing (COP) indication using the extracted feature, the COP indication indicating pacing at a rate higher than a pre-determined pacing rate threshold above a base pacing rate for an extended time period; and
adjusting a pacing therapy parameter in response to the detected COP indication.

14. The method of claim 13, wherein the pacing rate distribution includes a pacing rate histogram representing a relative number of paced heart beats with pacing rates falling into each of a plurality of pacing rate bins.

15. The method of claim 14, wherein extracting the feature includes a peak density of the pacing rate histogram, and detecting the COP indication if the peak density includes at least two histogram peaks.

16. The method of claim 14, wherein extracting the feature includes a morphological pattern of one or more histogram peaks.

17. The method of claim 16, wherein the morphological pattern includes a slope of the pacing rate histogram across pacing rate bins, and detecting the COP using a change in slope direction of the pacing rate histogram.

18. The method of claim 13, comprising wherein:
receiving the pacing rates of the paced heart beats include includes receiving sensor-indicated pacing rates according to a sensor response factor indicative of a degree of pacing rate increase at elevated patient metabolic demand; and
adjusting the pacing therapy parameter includes reducing the sensor response factor in response to the detected COP indication.

19. The method of claim 13, comprising detecting an atrial tachyarrhythmia, and switching to a non-atrial-tracking pacing mode in response to a detection of atrial tachyarrhythmia.

20. The method of claim 13, further comprising:
receiving information about patient physical activity during the cardiac pacing computing a correlation between the pacing rate distribution and the information about patient physical activity; and
adjusting a therapy using the correlation between the pacing rate distribution and the information about patient physical activity.

* * * * *